United States Patent
Weyler et al.

(10) Patent No.: US 6,642,031 B2
(45) Date of Patent: *Nov. 4, 2003

(54) MICROORGANISMS WITH ABILITY TO DEGRADE INDOLE AND ENZYMES THEREFROM

(75) Inventors: Walter Weyler, San Francisco, CA (US); Sol M. Resnick, Solana Beach, CA (US)

(73) Assignee: Genencor International, Inc., Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 126 days.

(21) Appl. No.: 09/570,779

(22) Filed: May 14, 2000

(65) Prior Publication Data

US 2003/0054519 A1 Mar. 20, 2003

Related U.S. Application Data

(63) Continuation of application No. 08/858,663, filed on May 19, 1997, now abandoned, which is a continuation of application No. 08/719,381, filed on Sep. 25, 1996, now abandoned, which is a continuation-in-part of application No. 08/560,729, filed on Nov. 20, 1995, now Pat. No. 6,190,892.

(51) Int. Cl.[7] .............................. C12N 1/20; C12P 21/00
(52) U.S. Cl. .................... 435/71.1; 435/69.1; 435/68.1; 435/243; 435/252.1; 435/253.3; 530/350
(58) Field of Search .............................. 435/243, 252.1, 435/253.3, 69.1, 68.1, 71.1; 530/350

(56) References Cited

FOREIGN PATENT DOCUMENTS

| EP | 288092 A | 10/1988 |
|---|---|---|
| EP | 336719 A | 10/1989 |
| WO | WO 94 08035 A | 4/1994 |
| WO | WO 9719175 A | 5/1997 |

OTHER PUBLICATIONS

Axcell, et al., Purification and Some Properties of a Soluble Benzene–Oxidizing System from a Strain *Biochem. J.* 146:173 (1975).
Berka, et al., "Studies of Phospholipase C (Heat–Labile Hemlysin) in *Pseudomonas aeruginos*, " *Infection and Immunity* 34:1071 (1981).
Ensley, et al., "Oxidation of Naphthalene by a Multicomponent Enzyme System from *Pseudomonas sp*, Strain NCIB 9816," *J. Bacteriol.* 149:948 (1982).
Ensley, et al., "*Naphthalene Dioxygenase* from Pseudomonas NCIB 9816," *Methods in Enzymology* 188:46 (1982).
Ensley, et al., "Expression of naphthalene oxidation genes in *Escherichia coli* results in the biosynthesis of indigo," *Science*, V. 222, pp. 167–169, Oct. 14, 1983, Lancaster, PA.
Gibson, et al., "Desaturation, Dioxygenation, and Monooxygention Reactions Catalyzed by Naphthalene Dioxygenase from *Pseudomonas sp.* Strain 9816–4," *J. Bacteriol.* 177:2615 (1995).
Haddock, et al., "Oxidation of Biphenyl by a Multicomponent Enzyme System from *Pseudomonas sp.* Strain LB400," *J. Bacteriol.* 175:395 (1993).
Hart, et al., "Construction of an insertional–inactivation cloning vector for *Escherichia coli* using a Rhodococcus gene for indigo production," *Journal of General Microbiology*, V. 138, N. 1, pp. 205–209, 1991.
Jeffrey, et al., "Initial Reactions in the Oxidation of Naphthalene by *Pseudomonas putida*," *Biochemistry* 11:575 (1975).
Pittard, A.J., *Biosynthesis of Aromatic Acids in Escherichia coli and Salmonella typhimurium*, F.C. Neidhardt, Ed., American Society for Microbiology, pp 368–394 (1987).
Resnick, et al., "Regiospecific and Stereoselective Hydroxylation of 1–Indanone and 2–Indanone by Naphthalene Dioxygenase and Toluene Dioxygenase," *Appl. Environ. Microl.* 60:3323 (1994).
Rogers and Gibson, "Purification and Properties of cis–Toluene Dihydrodiol Dehydrogenase from *Pseudomonas Putida*," *J. Bacteriol.* 130:1117 (1977).
Weyler, et al., "Isolation of a Pseudomonas putida, designated strain WW2, with an indole assimilatory pathway: Identification and cloning of isatin hydrolase, a novel assimilatory pathway enzyme," *Abstracts of the General Meeting of the American Society for Microbiology*, V. 96, N. 0, pp. 555, See Abstract No. K–118, 1996.
Yeh, et al., "Toluene Dioxygenase: A Multicomponent Enzyme System," *Biochem. Biophys, Res. Commun.* 78:401 (1977).

*Primary Examiner*—Sean McGarry
(74) *Attorney, Agent, or Firm*—Richard T. Ito

(57) ABSTRACT

There is provided novel indole oxidase activity isolated from *P. putida*, such indole oxidase activity is believed to be useful in the biosynthetic production of indigo from its precursor indole. Also provided are compositions of matter comprising the indole oxidase and methods for producing such.

6 Claims, 5 Drawing Sheets

MICROORGANISMS WITH ABILITY TO DEGRADE INDOLE AND ENZYMES THEREFROM

CROSS-REFERENCE TO RELATED APPLICATIONS

This application is a continuation application of U.S. application Ser. No. 08/858,663, filed May 19, 1997 now abandoned, which is a continuation application of U.S. application Ser. No. 08/719,381 filed Sep. 25, 1996 now abandoned, which is a continuation-in-part of U.S. application Ser. No. 08/560,729 filed Nov. 20, 1995, now U.S. Pat. No. 6,190,892 and which are incorporated herein by reference in their entirety.

FIELD OF THE INVENTION

The present invention relates to the isolation of a novel Pseudomonas species and identification of novel heterocyclic dioxygenases derived from this organism. The heterocyclic dioxygenase described herein is useful in the production of indigo in recombinant organisms.

BACKGROUND OF THE INVENTION

Pseudomonads are a diverse group of organisms capable of mineralizing biotic (e.g., camphor), xenobiotic (various chlorophenyl and biphenyl compounds) and fossil organic molecules (such as toluene or naphthalene). These capabilities are usually encoded by groups of genes collected in operons on extrachromosomal elements. A number of different enzyme classes are involved in the initial oxidation of these compounds. For example, camphor is degraded by a P450 monooxygenase while toluene, chlorobiphenyl and biphenyl, and naphthalene are oxidized by aromatic dioxygenases.

In the era of molecular biology, it was discovered that when certain aromatic dioxygenases were cloned into *Escherichia coli* and these were subsequently grown on a rich medium, colonies turned blue. It was later determined that the blue color was due to the conversion of tryptophan in the medium to indole by *E. coli* tryptophanase and its subsequent oxidation by the aromatic dioxygenases to indolediol, which in turn, in the presence of molecular oxygen, spontaneously further oxidized to indigo, leading to the observed blue coloration. Dioxygenases whose primary substrates are heterocyclic compounds, particularly where the substrate is indole, have not previously been characterized in detail. The heterocyclic dioxygenase reported here is capable of indole oxidation, leading to indigo formation.

The blue dye indigo is one of the oldest dyestuffs known to man. Its use as a textile dye dates back to at least 2000 BC. Until the late 1800s indigo, or indigotin, was principally obtained from plants of the genus Indigofera, which range widely in Africa, Asia, the East Indies and South America. As the industrial revolution swept through Europe and North America in the 1800s, demand for the dye's brilliant blue color led to its development as one of the main articles of trade between Europe and the Far East. In 1883, Adolph von Baeyer identified the formula of indigo: $C_{16}H_{10}N_2O_2$. In 1887, the first commercial chemical manufacturing process for indigo was developed. This process, still in use today, involves the fusion of sodium phenylglycinate in a mixture of caustic soda and sodamide to produce indoxyl. The process' final product, indoxyl, oxidized spontaneously to indigo by exposure to air.

Current commercial chemical processes for manufacturing indigo result in the generation of significant quantities of toxic waste products. Obviously, a method whereby indigo may be produced without the generation of toxic by-products is desirable. One such method which results in less toxic by-product generation involves indigo biosynthesis by microorganisms.

Ensley et al. ((1983) *Science* 222:167–169) found that a DNA fragment from a transmissible plasmid isolated from the soil bacterium *Pseudomonas putida* enabled *Escherichia coli* that had been stably transformed with a plasmid harboring the fragment to synthesize indigo in the presence of indole or tryptophan. Ensley et al. postulated that indole, added either as a media supplement or produced as a result of enzymatic tryptophan catabolism, was converted to cis-indole-2,3-dihydrodiol by the previously identified multi-component-enzyme naphthalene dioxygenase (NDO) encoded by the *P. putida* DNA fragment. The indole-2,3-dihydrodiol so produced spontaneously lost water forming indoxyl and was then oxidized to indigo upon exposure to air.

NDO had previously been found to catalyze the oxidation of the aromatic hydrocarbon naphthalene to (+)-cis-(1R,2S)-dihydroxy-1,2-dihydronaphthalene (Ensley et al. (1982) *J. Bacteriol.* 149:948–954). U.S. Pat. No. 4,520,103, incorporated by reference, describes the microbial production of indigo from indole by an aromatic dioxygenase enzyme such as NDO. The NDO enzyme is comprised of multiple components: a reductase polypeptide (Rd, molecular weight of approximately 37,000 daltons (37 kD)); an iron-sulfur ferredoxin polypeptide (Fd, molecular weight of approximately 13 kD); and a terminal oxygenase iron-sulfur protein (ISP). ISP itself is comprised of four subunits having an $\alpha_2\beta_2$ subunit structure (approximate subunit molecular weights: $\alpha$, 55 kD; $\beta$, 21 kD). ISP is known to bind naphthalene, and in the presence of NADH, Rd, Fd and oxygen, to oxidize it to cis-naphthalene-dihydrodiol. Fd is believed to be the rate-limiting polypeptide in this naphthalene oxidation catalysis, (see U.S. Pat. No. 5,173,425, incorporated herein by reference, for a thorough discussion of the various NDO subunits and ways to improve them for purposes of indigo biosynthesis).

In addition, aromatic dioxygenases other than NDO may also be useful in the biosynthetic production of indigo, for example, a toluene monooxygenase (TMO) such as that from Pseudomonas (*P. mendocina*) capable of degrading toluene was also able to produce indigo when the culture medium was supplemented with indole. For details, see U.S. Pat. No. 5,017,495, incorporated herein by reference. In principle, any enzyme capable of introducing a hydroxyl moiety into the 3-position of indole to give indoxyl is a candidate for use in the biosynthetic production of indigo. This includes single component flavin containing monooxygenases.

Most, if not all, oxygenases described in the art for use in oxidation of the substrate indole, as for example in the production of indigo, are aromatic oxygenases. While these enzymes have been successfully employed in the synthesis of indigo, there is a need for an enzyme or class of enzymes which have as a primary substrate heterocyclic compounds such as indole. Such heterocyclic oxygenases are believed to be advantageous over aromatic oxygenases in oxidizing indole and ultimately in indigo production.

DEFINITION OF TERMS

The following terms will be understood as defined herein unless otherwise stated. Such definitions include without recitation those meanings associated with these terms known to those skilled in the art.

Tryptophan pathway genes useful in securing biosynthetic indole accumulation include a trp operon, isolated from a microorganism as a purified DNA molecule that encodes an enzymatic pathway capable of directing the biosynthesis of L-tryptophan from chorismic acid. (A. J. Pittard (1987) *Biosynthesis of Aromatic Amino Acids in Escherichia coli and Salmonella typhimurium*, F. C. Neidhardt, ed., American Society for Microbiology, publisher, pp. 368–394.) Indole accumulation is enabled by modification of one or more of the pathway's structural elements and/or regulatory regions. This modified trp operon may then be introduced into a suitable host such as a microorganism, plant tissue culture system or other suitable expression system. It should be noted that the term "indole accumulation" does not necessarily indicate that indole actually accumulates intracellularly. Instead, this term can indicate that there is an increased flux of carbon to indole and indole is made available as a substrate for intracellular catalytic reactions such as indoxyl formation and other than the formation of L-tryptophan. In the context of this invention, the "accumulated" indole may be consumed in the conversion of indole to indoxyl by an oxygenase such as the aromatic dioxygenase NDO, or an aromatic monooxygenase such as TMO, or it may actually build up intracellularly and extracellularly, as would be the case when the desired end product is indole or one of its derivatives.

A suitable host microorganism or host cell is an autonomous single-celled organism useful for microbial indole and/or indigo production and includes both eucaryotic and procaryotic microorganisms. Such host microorganism contains all DNA, either endogenous or exogenous, required for the production of indole, indoxyl and/or indigo, from glucose, as a bioconversion from tryptophan, or, in the case of producing indoxyl or indigo, from indole. Useful eucaryotes include organisms like yeast and fungi or plants. Prokaryotes useful in the present invention include, but are not limited to, bacteria such as *E. coli, P. putida* and *Salmonella typhimurium*.

Biosynthetic conversion of indole to indigo is meant to include indoxyl oxidation to indigo mediated by molecular oxygen or air.

A DNA fragment, as used herein, may encode regulatory and/or structural genetic information. A DNA fragment useful in the present invention shall also include: nucleic acid molecules encoding sequences complementary to those provided; nucleic acid molecules (DNA or RNA) which hybridize under stringent conditions to those molecules that are provided; or those nucleic acid molecules that, but for the degeneracy of the genetic code, would hybridize to the molecules provided or their complementary strands. "Stringent" hybridization conditions are those that minimize formation of double stranded nucleic acid hybrids from non-complementary or mismatched single stranded nucleic acids. In addition, hybridization stringency may be affected by the various components of the hybridization reaction, including salt concentration, the presence or absence of formamide, the nucleotide composition of the nucleic acid molecules, etc. The nucleic acid molecules useful in the present invention may be either naturally or synthetically derived.

A "heterologous or exogenous" DNA fragment is one that has been introduced into the host microorganism by any process such as transformation, transfection, transduction, conjugation, electroporation, etc. Additionally, it should be noted that it is possible that the host cell into which the "exogenous" DNA fragment has been inserted may itself also naturally harbor molecules encoding the same or similar sequences. For example, when *E coli* is used in this invention as the host strain, it is recognized that, normally, the host naturally contains, on its chromosome, a trp operon capable of directing the synthesis of L-tryptophan from chorismic acid under conditions enabling trp operon expression. A molecule such as this is referred to as an "endogenous" DNA molecule.

A stably transformed microorganism is one that has had one or more exogenous DNA fragments introduced such that the introduced molecules are maintained, replicated and segregated in a growing culture. Stable transformation may be due to multiple or single chromosomal integration(s) or by extrachromosomal element(s) such as a plasmid vector (s). A plasmid vector is capable of directing the expression of polypeptides encoded by particular DNA fragments. Expression may be constitutive or regulated by inducible (or repressible) promoters that enable high levels of transcription of functionally associated DNA fragments encoding specific polypeptides such as the structural genes of a trp operon modified as described herein.

An "isatin-removing enzyme," as used herein, is any enzyme which comprises activity resulting in the inhibition, removal, inactivation, degradation, hydrolysis or binding (sequestering) of isatin, whether such enzyme causes the formation of isatic acid or any other degradation product. A preferred isatin-removing enzyme useful in the present invention is an isatin hydrolase such as the hydrolase isolated from *Pseudomonas putida* (WW2) herein, deposited in accordance with the Budapest Treaty on International Recognition of the Deposits of Microorganisms for the Purpose of Patent Procedures as Deposit ATCC #55763.

Regardless of the exact mechanism utilized for expression of enzymes necessary for the microbial production of indole, indoxyl and/or indigo, it is contemplated that such expression will typically be effected or mediated by the transfer of recombinant genetic elements into the host cell. Genetic elements as herein defined include nucleic acids (generally DNA or RNA) having expressible coding sequences for products such as proteins, specifically enzymes, apoproteins or antisense RNA, which express or regulate expression of relevant enzymes (i.e., isatin hydrolase, tryptophan synthase, NDO, etc.). The expressed proteins can function as enzymes, repress or derepress enzyme activity or control expression of enzymes. Recombinant DNA encoding these expressible sequences can be either chromosomal (integrated into the host cell chromosome by, for example, homologous recombination) or extrachromosomal (for example, carried by one or more plasmids, cosmids and other vectors capable of effecting the targeted transformation). It is understood that the recombinant DNA utilized for transforming the host cell in accordance with this invention can include, in addition to structural genes and transcription factors, expression control sequences, including promoters, repressors and enhancers, that act to control expression or derepression of coding sequences for proteins, apoproteins or antisense RNA. For example, such control sequences can be inserted into wild-type host cells to promote overexpression of selected enzymes already encoded in the host cell genome, or alternatively they can be used to control synthesis of extrachromosomally encoded enzymes.

The recombinant DNA can be introduced into the host cell by any means, including, but not limited to, plasmids, cosmids, phages, yeast artificial chromosomes or other vectors that mediate transfer of genetic elements into a host cell. These vectors can include an origin of replication, along with cis-acting control elements that control replication of the vector and the genetic elements carried by the vector. Selectable markers can be present on the vector to aid in the identification of host cells into which genetic elements have been introduced. Exemplary of such selectable markers are genes that confer resistance to particular antibiotics such as tetracycline, ampicillin, chloramphenicol, kanamycin or neomycin.

A means for introducing genetic elements into a host cell utilizes an extrachromosomal multi-copy plasmid vector into which genetic elements in accordance with the present invention have been inserted. Plasmid borne introduction of the genetic element into host cells involves an initial cleaving of a plasmid vector with a restriction enzyme, followed by ligation of the plasmid and genetic elements encoding for the targeted enzyme species in accordance with the invention. Upon recircularization of the ligated recombinant plasmid, infection (e.g., packaging in phage lambda) or other mechanism for plasmid transfer (e.g., electroporation, microinjection, etc.) is utilized to transfer the plasmid into the host cell. Plasmids suitable for insertion of genetic elements into the host cell are well known to the skilled artisan.

SUMMARY OF THE INVENTION

The present invention provides a novel microorganism of the genus Pseudomonas, the species of which is preliminarily identified as a putida, and strain designation WW2. The designation therefore is *Pseudomonas putida* strain WW2. This strain has been deposited at the American Type Culture Collection, Rockville, Md. as strain ATCC #55763.

Also provided is an enzyme isolated from *P. putida* WW2 which is an indole oxidase, as well as methods for producing the oxidase and compositions of matter comprising the oxidase as a single component Indole is the primary substrate for this enzyme expressed from WW2 since the organism can grow on indole as the sole substrate providing carbon, nitrogen and energy. This enzyme is hereafter referred to as an indole oxidase or dioxygenase and has the following physio-chemical properties: (a) enzyme action: catalyzes in presence of NADH or NADPH and FAD as a cofactor, the oxidation of indole to indoxyl or indolediol; and (b) pH optimum of from about 7–9, preferably 8.0.

A further aspect of this invention is the use of the indole oxidase or dioxygenase to oxidize indole toga precursor which spontaneously converts to indigo. Thus, there is provided an improved method for the biocatalytic production of indigo in a suitable host-microorganism. Suitable host microorganisms include but are not limited to host organism(s) expressing (either exogenously or endogenously) indole oxygenase activity and/or isatin hydrolase activity. Such organisms are cultivated under conditions facilitating the expression of the indole oxidase activity and/or isatin hydrolase. By way of example, a suitable microorganism could be *P. putida* ATCC #55763 which expresses endogenously both indole oxidase and isatin hydrolase activity. This embodiment preferably would include a modification of ATCC #55763 to block conversion of indole to compounds along its indole degradation pathway to compounds other than indigo. Similarly, a suitable host organism could express endogenously or exogenously any one or more of the enzymatic activities necessary to convert glucose, tryptophan (tryptophanase) or indole (indole oxidase) to indigo. As such, a suitable host organism could be a procaryote or eucaryote transformed or transfected with DNA encoding one or more of the following: shikimic acid pathway enzymes, indole oxidase, a tryptophan operon (or modified operon) and/or isatin hydrolase.

The oxidase enzyme of the present invention is a multi-component enzyme that can utilize nicotinamide adenine dinucleotide (NADH) or nicotinamide adenine phosphate dinucleotide (NADPH), requires flavin adenine dinucleotide (FAD) and its activity is stimulated by the presence of iron in a cell-free extract.

The enzyme has very low activity with naphthalene, indicating significant differences between the present enzyme and naphthalene dioxygenase previously reported in the production of indigo in *E coli*.

Another aspect of the present invention is the cloning and sequencing of the gene encoding a preferred oxidase enzyme, indole oxidase.

DETAILED DESCRIPTION OF THE INVENTION

Figure 1:
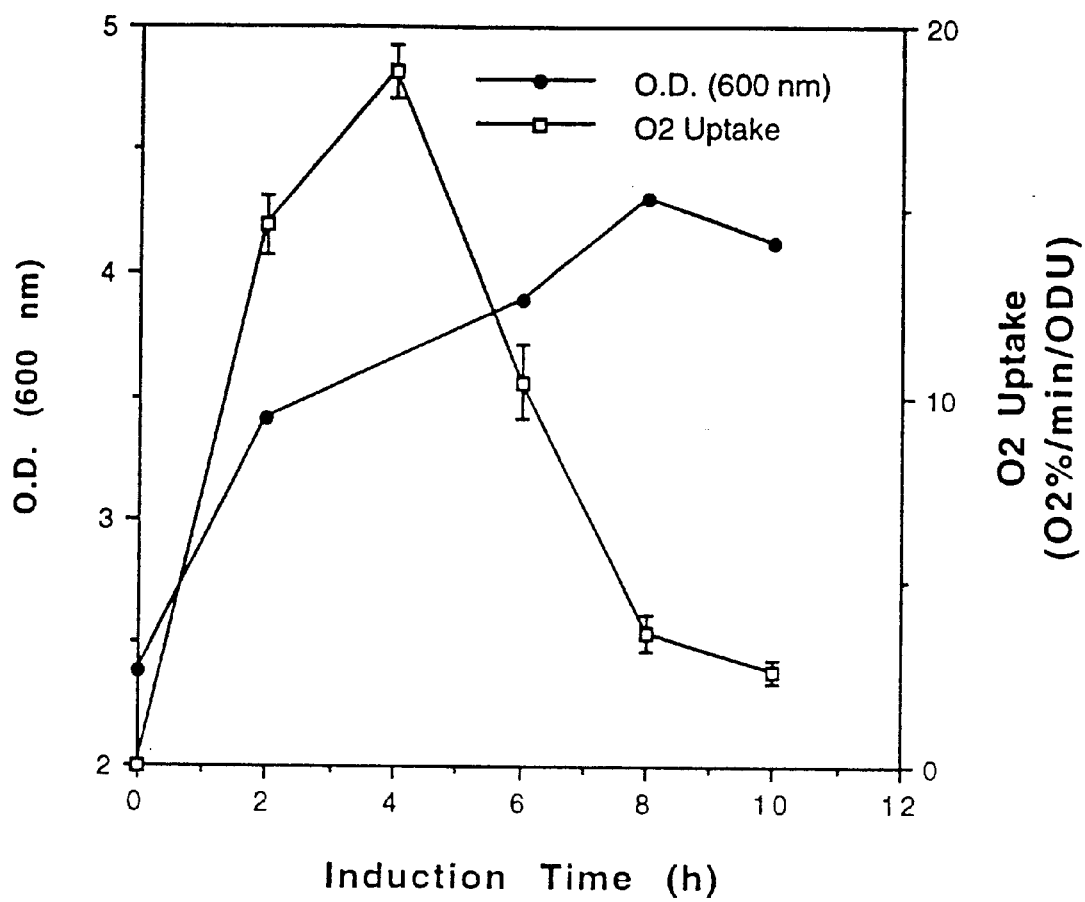
FIG. 1 shows the indole oxidase activity and growth of *P. putida* strain WW2 in MSB/succinate induced with indole.

*P. putida* (ATCC #55763) isolated from a soil sample as previously described produces several enzymes useful for degrading indole. A suggested pathway of indole degradation by *Pseudomonas putida* WW2 is provided in Scheme A below.

Scheme A

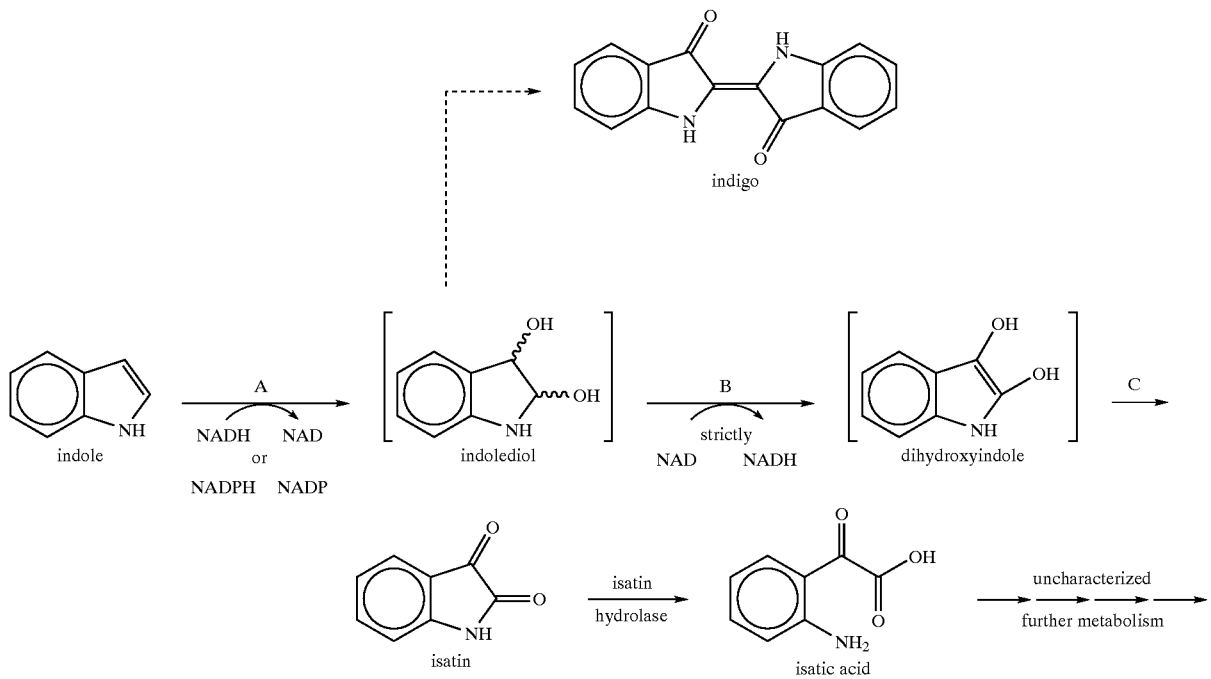

A, is suggested to be a multicomponent (two or more components indicated by enzyme kinetic experiments) heteroaromatic oxidase or dibxygenase which is specific for indole. This multicomponent enzyme is the subject matter of the present application. B and C are dehydrogenases. The fourth enzyme in the proposed pathway is an isatin hydrolase as previously identified, cloned and partially characterized. Metabolic steps after isatic acid formation are not known, but presumably lead to the primary metabolites succinate and acetate. The bracketed structures have not been identified.

Isolation, characterization and general growth conditions of the microorganism. The novel organism of the present invention was isolated from enrichment cultures containing soil from a creosote manufacturing site in Terre Haute, Ind. There was no obvious gross contamination of the soil sample with fossil fuel residues. A pure culture of the isolated microorganism designated *Pseudomonas putida* strain WW2 was deposited with the ATCC in Rockville, Md. as #55763 according to the Budapest Treaty on the International. Recognition of the Deposits of Microorganisms for the Purpose of Patent Procedures. Young colonies of the organism growing on minimal agar with indole as the sole carbon source will turn blue when exposed to 5-fluoroindole. The blue color has not been characterized but is presumably 5,5'-difluoroindigo.

Classification and identification of the microorganism. The strain was characterized by analysis of substrate utilization (Biolog) and fatty-acid methyl ester (MIDI) profiles (both performed by Microbe Inotech Laboratories, 1840 Craig Road, St. Louis, Mo. 63146–4712) and by analysis for phospholipase C activity (Berka, R. M., G. L. Gray, M. L. Vasil (1981) "Studies of phospholipase C (heat-labile hemolysin in *Pseudomonas aeruginosa*)," *Infection and Immunity* 34:1071–1074) and gelatin-liquefaction assays (Krieg, R. N., ed. (1984) *Bergey's Manual of Systematic Bacteriolog*, vol.1 (Holt, J. G. series ed.), pp. 163–165, Williams and Wilkins, Baltimore). Biolog analysis indicates close similarity with *Pseudomonas marginalis* while MIDI analysis indicates similarity with *Pseudomonas putida* (results of Biolog and MIDI analysis not shown). Gelatin liquefaction assays and phospholipase C assays were both negative, indicating that the relationship is closer to putida. In addition, 16S rRNA analysis supports the classification of putida. A unique characteristic of the strain is its production of an enzyme that hydrolyzes isatin (2,3-dioxoindole) to isatic acid (2-(2-aminophenyl)-2-oxoacetic acid). This enzyme, presumed to be required for growth on indole, is described in copending application U.S. Ser. No. 08/560,729 filed Nov. 20, 1995.

Cultivation of the organism. Growth was measured turbidimetrically at 600 nm. The organism was initially isolated by enrichment culture in a mineral salts medium (MSB, pH 7.2) (Stanier, R. Y., N. J. Palleroni, M. Doudoroff (1966) "The aerobic Pseudomonads; a taxonomic study," *J. Gen. Microbiol.* 43:159–271) containing 0.02% indole as carbon source for growth and 0.005% yeast extract Biolog analysis revealed a number of suitable nutrients (data not shown). The organism grew well on a rich medium such as Luria Broth at 30° C. Additional potential carbon sources were assessed in MSB supplemented with the carbon alternate source (0.2% (w/v) unless specified otherwise) or on plates provided with volatile substrates in the vapor phase. Growth was also conducted in 14 L fermenters in the fed batch mode. In liquid culture, indole was a good carbon source but was toxic when its concentration exceeded 400 mg/L. Naphthalene did not support growth at any concentration. To study enzyme activity of indole oxidase, the organism was cultured in 50 or 500 ml of media (in 250 ml or 2.8 L nominal volume flasks, respectively) containing minimal salts, succinate and 0.02% indole at 30° C. with rotary shaking (200 rpm).

Enzyme activity. Initially, indole oxidase activity was measured as indole-dependent oxygen uptake by whole cells measured with a Clark-type electrode in an oxygraph cell. Induction of indole oxidase activity required the presence of indole. Activity was rapidly lost upon disappearance of indole from the medium. In addition, in the absence of indole, isatin hydrolase activity was produced at 1/20 the level compared to when cells were grown in the presence of indole. This activity was measured in a spectrophotometric assay by monitoring either disappearance of absorbance at 308 nm due to hydrolysis of isatin or appearance of absorbance at 368 due to the formation of the product, isatic acid. Indole oxidase activity has been partially purified from a cell extract by ion exchange chromatography. No individual fraction from such a chromatography experiment exhibits indole-dependent oxygen uptake in the oxygraph or by measuring NADH oxidation spectrophotometrically, but requires the mixing of at least two fractions. This indicates that the activity requires at least two protein components separated by the column. When NADPH is substituted, indole disappears again, but 20% of the starting material consumed can be accounted for by formation of indigo.

It is proposed that the indole oxidase identified from WW2 may be cloned and used for the production of indigo. This enzyme may perform in a superior manner over naphthalene dioxygenase and other aromatic amine oxygenases of the prior art since indole is the preferred substrate for the enzyme of the present invention. One difficulty encountered with prior art naphthalene dioxygenase is its catalytic inactivation under conditions of enzyme turnover. While this type of inactivation is observed with a number of dioxygenases, it is known to those familiar with the art that poor substrates can uncouple reduction of molecular oxygen from hydroxylation of the substrate, leading to the production of active oxygen species which can modify amino acid residues of these enzymes, thereby inactivating the enzyme. Since indole is the natural substrate for the oxidase enzyme of this invention, it is expected that uncoupling and inactivation will be minimized. Lower inactivation rate should, in turn, require lower protein expression levels, leading to a healthier production organism with better metabolic stability and extended productive phase of a fermentation.

The genes for the indole oxidase may be isolated by cosmid cloning. Selection for the specific genes can be by observation of blue colonies formed in the cosmid cloning host. Alternatively, oxidase genes can be identified by transposon mutagenesis. With this technique, mutants of *Pseudomonas putida* strain WW2 interrupted in the indole oxidase operon can be identified due to inability to grow on indole but forming blue colonies when cells are grown on a metabolizable carbon source, such as succinate, followed by exposure to indole vapor. Mutants forming blue colonies are predicted to have a block due to transposon insertion into the operon at the first enzyme after the oxidase. Numerous colonies of such phenotype have been isolated by this technique and they are being characterized. The antibiotic marker on the transposon would be used to isolate the appropriate DNA fragments. DNA obtained from either method may be sequenced by standard methods to identify open reading frames. Even though the expected enzyme is unique in its activity, it is anticipated that common sequence motives, such as motives for iron sulfur centers, would allow the identification of oxidase components. These would be mapped to identify unique restriction sites and cloned into vectors already in use for biosynthetic indigo production. The vectors containing the indole oxidase genes can then be transformed into appropriate hosts to test their efficacy as indigo producers. Appropriate vectors and/or host organisms are as described in U.S. patent application Ser. No. 08/560,729.

EXPERIMENTAL

Materials and Methods

General methods utilized in the Experimental section are described in this Materials and Methods section.

Spectrophotometric assays. Cell-free, indole-dependent NADH oxidation was measured spectrophotometrically with a Hewlett-Packard 8452A diode array spectrophotometer. The reactions (1.0 ml volume) contained crude soluble cytosolic fraction (SCF), 3.0 mM NADH, 2.0 mM indole and 50 mM Tris-HCl (pH 7.5). The reactions were initiated by addition of NADH and the initial rates were corrected for background NADH oxidation rates, which were measured in the absence of indole. NADPH was substituted for NADH to compare its ability to serve as an electron donor for indole oxidation activity.

Cytochrome c reduction activity. Cytochrome c reduction activity of fractions from ion exchange chromatography (described below) was measured as previously described (Ensley, B. D. and B. E. Haigler (1990) "Naphthalene dioxygenase from Pseudomonas NCIB 9816," *Methods in Enzymology* 188:46–52). The assay was adapted to 96-well microtiter plates (200 μl reaction volume) in order to rapidly locate cytochrome c reduction activity in column fractions. Assays were initiated by adding a freshly prepared mixture consisting of 88 nmol of horse heart cytochrome c (Sigma), 300 nmol NADH, 1.0 nmol FAD in 50 mM Tris-HCl (pH 7.5) to microtiter wells containing 2 to 10 μl of the fraction being screened.

Substrate depletion assays. Substrate depletion assays were carried out in 1.5 ml to 10 ml reactions containing crude SCF, 4.0 mM NADH or NADPH, 2.0 μM FAD, and 1.0 mM indole in 50 mM Tris-HCl (pH 7.5 or 8.0). Substrate and product concentrations were determined by incubating the reactions for the specified period of time with shaking at 250 rpm, extracting 1.0 ml of the aqueous reaction with ethyl acetate and analyzing the extract by gas chromatography-mass spectrometry (GC/MS) described below.

GC/MS methods. GC/MS was carried out with a Hewlett-Packard model 5890 gas chromatograph equipped with a Hewlett-Packard DB-5 capillary column (inside diameter 0.2 mm by 25 m) and a Hewlett-Packard model 5971 mass selective detector (electron impact ionization 70 eV). The column temperature was programmed from 50 to 325° C. at 10° C./min with a helium flow of 12 cm/s. Temperatures of the injection port and transfer line were 250 and 280° C., respectively. Under these conditions, the standards for indole, oxindole, indene, 1-indenol, 1-indanone and 2-indanone eluted with retention times of 8.68, 11.25, 4.91, 7.76, 8.26 and 7.55 min, respectively.

EXAMPLE 1

Isolation of Organisms Capable of Growth on Indole as Sole Carbon Source

Soil samples derived from 13 widely dispersed locations in the US were processed by an enrichment protocol in a mineral salts medium (MSB, pH 7.2) (Stanier, R. Y., N. J. Palleroni, M. Doudoroff (1966) "The aerobic Pseudomonads; a taxonomic study," *J. Gen. Microbiol.* 43:159–271) containing 0.02% indole as carbon source for growth and a trace (0.005%) of yeast extract to complement potential vitamin requirements. After three sequential passages into fresh medium and sequential rounds of plating on solid medium (addition of 1.5% agar to liquid medium) of the same nutrient and buffer composition, Luria broth agar without indole, and again MSB solid medium with agar, 8 cultures could be purified. On MSB plates, three clear phenotypes could be distinguished. The fastest growing culture, designated WW2, was further analyzed. The remaining cultures were frozen for future examination.

EXAMPLE 2

Classification of *Pseudomonas putida* Strain
*Pseudomonas putida* Strain WW2

A pure culture from Example 1, first designated WW2 and derived from a soil sample from a creosote manufacturing site in Terre Haute, Ind., was characterized by analysis of substrate utilization (Biolog) and fatty-acid methyl ester (MIDI) profiles, as well as by phospholipase C (Berka, R. M., G. L. Gray, M. L. Vasil (1981) "Studies of phospholipase C (heat-labile hemolysin in *Pseudomonas aeruginosa*)," *Infection and Immunity* 34:1071–1074) and gelatin-liquefaction assays (Krieg, R. N., ed. (1984) *Bergey's Manual of Systematic Bacteriology*, vol. 1 (Holt, J. G. series ed.), pp. 163–165, Williams and Wilkins, Baltimore). The latter two test were negative. In addition, 16S rRNA analysis was carried out. The combined results indicate the strain to be a *Pseudomonas putida* which we then designated *Pseudomonas putida* strain WW2. This strain has been deposited with the American Type Culture Collection as ATCC #55763.

EXAMPLE 3

Induction of Indole Oxidase/Hydroxylase Activity

Several methods were examined to induce cultures of strain *Pseudomonas putida* WW2 for indole oxidation during growth. These included growing the strain in MSB containing 0.2% succinate with: (i) a single addition of 0.02% indole and 0.2% succinate during late log phase; (ii) indole provided in the vapor phase, during growth, from a small cloth bag containing indole crystals suspended above the surface of the medium; or (iii) both indole vapor during growth and direct addition of 0.02% indole and 0.2% succinate during late log phase. Data from these experiments are summarized in Table 1 below.

TABLE 1

Sustained Indole Oxidation Activity
in Strain WW2 by Re-Addition of Indole[1]

| | Oxygen Uptake Rate ($O_2$ %/min/ODU) | |
|---|---|---|
| Re-Additions to 4 h Indole-Induced Cells | Rate After 4 h Induction with Indole | Rate 3 h After Re-Addition |
| No addition | 14.1 | 2.1 |
| Indole 0.2 g/l + Succinate 2 g/l | 12.1 | 12 |
| Indole 0.2 g/l | 14.4 | 13.8 |
| Succinate 2 g/l | 13.3 | 1.8 |

[1]Cultures of WW2 were grown in 50 ml MSB + 0.2% succinate, then induced with indole 0.2 g/l at 16 h growth. Re-additions were made 4 h after introduction of indole (i.e., at 20 h). Oxygen uptake with indole was measured 4 h and 7 h following the initial induction.

Figure 2:
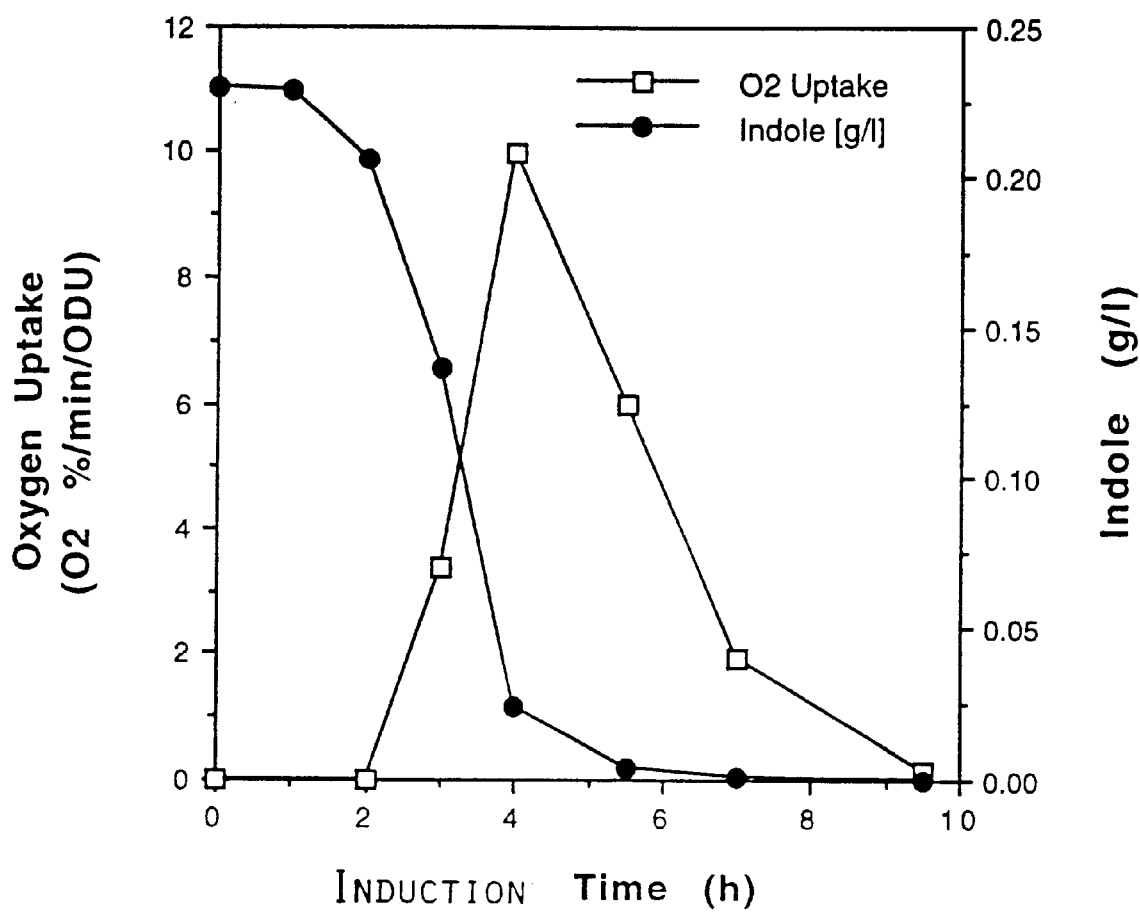
FIG. 2 shows the indole utilization and indole oxidation rate of *P. putida* strain WW2 during growth on MSB and succinate (0.4%).

The effect of subsequent indole and/or succinate additions on indole oxidation activity was also examined. These experiments led to the standard conditions for the induction of indole oxidation activity of strain WW2 and are as follows: overnight growth at 30° C. in 500 ml MSB containing 0.4% succinate (in 2.8 L Fernbach flasks) with a small cloth bag containing indole crystals (ca. 2 g) suspended above the surface of the medium. These conditions provided sufficient yields of cells (10 g wet cells/L) which had high indole oxidation activity as determined by oxygen uptake analysis described in Example 11. Quantitative studies indicated that indole oxidase activity was strongly dependent on the presence of indole in the growth medium. FIG. 2 shows that the decay of indole oxidation activity could be correlated to indole depletion from the culture medium. This is an interesting observation and suggests that the indole oxidase is tightly controlled at the level of synthesis and decay.

EXAMPLE 4

Expression of Isatin Hydrolase Activity

A 1:4 cell homogenate in 50 mM Tris-HCl, pH 7.5, of *P. putida* WW2 and grown either in LB medium containing 1.7 mM indole or in a minimal salt medium containing 1.7 mM indole was prepared by disrupting the cells inma French pressure cell. The homogenate was assayed directly or the supernatant and the pellet were assayed after 100,000 g centrifugation of the homogenates. Isatin hydrolase activity was found in the whole homogenates and in the high speed supernatants. Less than 5% of activity was detected in the high speed pellets. Equivalent activity was detected whether the cells were grown in rich or minimal medium. Cells grown in rich medium in the absence of indole had 20-fold reduced activity, indicating that indole or one of its metabolites induces the enzyme activity.

Apparent native molecular size was determined as follows. The crude homogenate from above was fractionated on DEAE cellulose with a 0 to 500 mM NaCl gradient in 50 mM Tris/HCl, pH 7.5. Enzymatic activity eluted at ~175 mM NaCl, however, 85% of the enzymatic activity was lost during this single step. Pooled and dialyzed fractions were further fractionated by a 30% to 40% $NH_4SO_4$ precipitation. Further losses in activity to about 10% of original activity resulted. Further treatment of the sample with TSK Q ion exchange chromatography yielded 1.4% of original activity on elution with a 0 to 500 mM NaCl gradient in the same buffer. This remaining activity was finally applied to a Sepharose S-100 gel filtration column. Enzymatic activity eluted corresponding to an apparent molecular weight of about 30 to 40,000 Da. Steps described above were monitored by spectrophotometric enzymatic assay. Either disappearance of isatin or appearance of isatic acid could be monitored at 302 or 368 $\mu$M, respectively, in 50 mM Tris/HCl, pH 7.5. Activity could also be detected on a 7.5% native acrylamide gel by overlaying the developed gel with a nitrocellulose membrane previously soaked in 5,7-dimethylisatin. Enzyme was located by the appearance of a white spot on the peach colored membrane, the color having been imparted by incubation of the membrane with a 3.5 mg/10 ml 50 mM Tris HCl pH 7.5, 5,7-dimethylisatin solution for 20 min.

EXAMPLE 5

Carbon Source Utilization and Oxygen Uptake Stimulation of Resting Cells

Carbon utilization of WW2 was determined by its ability to grow on alternate carbon sources. The bulk of these were determined by Biolog assay. In addition, naphthalene was found not to support growth when supplied to a culture inoculated with *Pseudomonas putida* strain WW2 in MSB liquid medium, or on agar plates. In addition, substrate-dependent oxygen consumption of whole resting cells was measured by oxygraph assay as described in Example 11. These data are summarized in Table 2 and are discussed briefly below.

TABLE 2

Strain WW2 Whole Cell Oxygen Uptake with Indole and Related Substrates[2]

| Substrate (0.6 mM) | Oxygen Uptake ($O_2$ %/min/ODU) | Relative % |
| --- | --- | --- |
| Indole | 11.8 | 100% |
| Oxindole | 1.1 | 9% |
| Anthranilate | 0.6 | <1% |
| Indoxyl (corrected) | 20.9 | 177% |
| 5-F-Indole | 5.9 | 50% |
| 7-Me-Indole | 4.6 | 39% |
| Naphthalene | 1.1 | 9% |
| Thianaphthene | 3.1 | 26% |
| 2,3-Benzofuran | 3.5 | 30% |

[2]Strain WW2 was grown in 50 ml MSB + 0.2% succinate and induced with indole 0.2 g/L + 0.2% succinate at 16 h growth. Oxygen uptake was measured 4.5 h following the indole induction as described in Materials and Methods.

Rate of indole-dependent oxygen uptake was defined as 100%. Indoxyl (3-hydroxyindole) showed a 1.7-fold increase in oxygen uptake rate, suggesting that this compound may be an intermediate on the indole degradative pathway. Oxindole (2-oxoindole) showed only a 9% rate, suggesting it to be off the pathway of indole degradation. Anthranilic acid had no significant stimulation of oxygen uptake rate, suggesting that anthranilate is not an intermediate in indole degradation. In this assay naphthalene showed a 9% rate stimulation. This clearly indicates that either the cell cannot take up napthalene or that naphthalene is a poor substrate for the enzyme. However, coupled with the low rate of naphthalene-dependent oxygen uptake in soluble cytosolic fraction, the data suggests that the putative indole oxidase/hydroxylase/dioxygenase is not an aromatic naphthalene dioxygenase. The remainder of compounds investigated in the whole cell assay are indole analogs and had $O_2$ uptake rates between 26 and 50%. These data will be useful in future comparisons with similar enzymes.

EXAMPLE 6

Enzyme Extraction

Crude cell extract was prepared from *Pseudomonas putida* strain WW2 cells induced per Example 3 by suspending cells (1:1, wet weight/vol) in 50 mM tris (hydroxymethyl)aminomethane (Tris-HCl, pH 7.5) containing 0.5 mM dithiothreitol (DTT), 3 mM $Mg^{++}$ and 10 µg/ml DNase I and by two passages of the suspension through a chilled French pressure cell at 20,000 lb/in$^2$. The homogenate was then diluted 1:1 with 50 mM Tris-HCl (pH 7.5) containing 0.5 mM DTT and centrifuged (100,000×g, 90 min) to obtain soluble cytosolic fraction (SCF). SCF was stored either on ice for immediate use or frozen at −80° C. for later use.

EXAMPLE 7

Characterization of Solubilized Indole OxidizinG Activity

Cofactor requirement of the indole oxidizing activity in the crude soluble cytosolic fraction was investigated in spectrophotometric assays as described in Example 6. Data obtained are summarized in Table 3.

TABLE 3

Cofactor Requirements for Indole Oxidation Activity in Strain WW2 Crude Cell Extract

| Assay Components[3] | | | | | | | NADH Oxidation | Activity |
| --- | --- | --- | --- | --- | --- | --- | --- | --- |
| Cell Extract | Indole | NADH | NADPH | FAD | FMN | $Fe^{2+}$ | A340 Rate[4] | Relative % Rate |
| + | + | + | − | − | − | − | 0.143 | 30% |
| + | + | + | − | + | − | − | 0.482 | 100% |
| + | + | − | + | + | − | − | 0.151 | 31% |
| + | + | + | − | − | + | − | 0.173 | 36% |
| + | + | + | − | − | − | + | 0.385 | 80% |

[3]Final concentrations in 1.0 ml assays were: cell extract, 0.91 mg protein/ml; indole, 0.5 mM; NADH and NADPH, 300 µM; FAD and FMN, 1 µM; Fe(NH$_4$)$_2$SO$_4$, 140 µM.
[4]Reported rates indicate the indole-dependent NAD(P)H oxidation activity and are the average of duplicate determinations.

Figure 3:
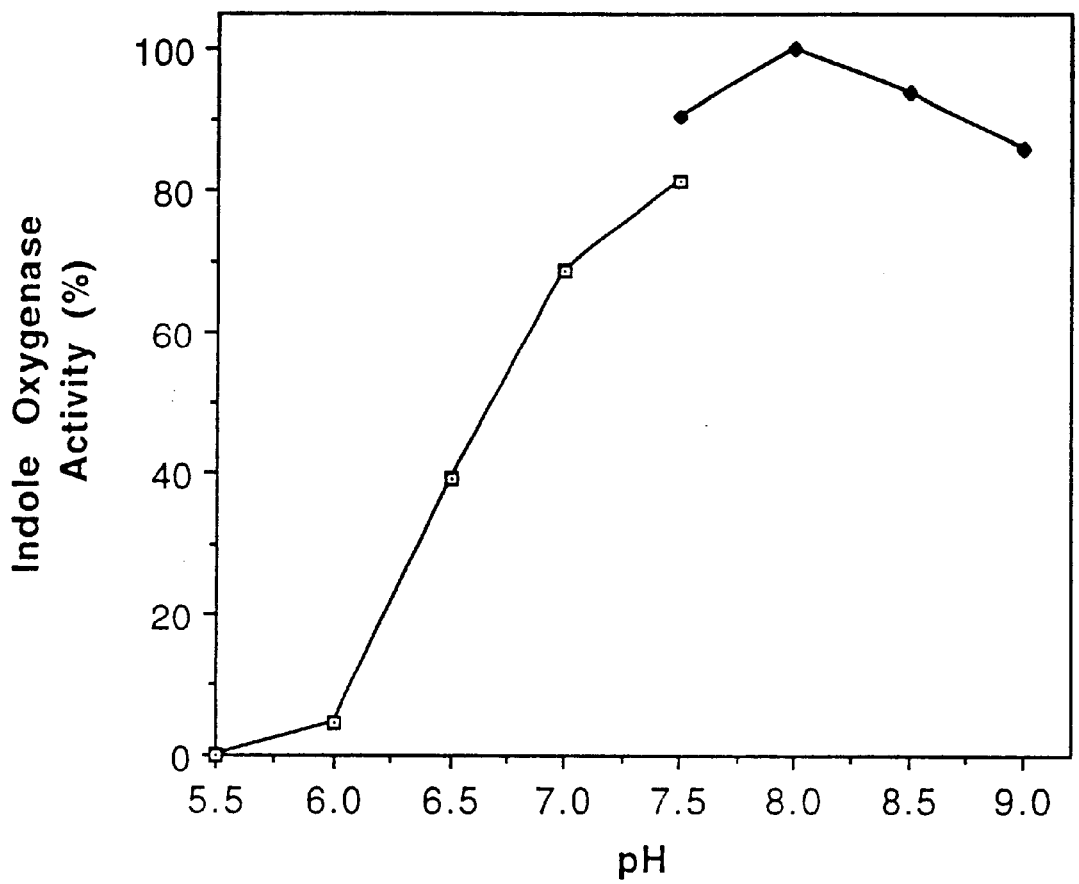
FIG. 3 shows the pH optimum of the heterocyclic (indole) oxygenase activity in crude cell extract of *P. putida* WW2.

There is a 3-fold preference of NADH over NADPH for source of reducing equivalents. FAD added to the assay stimulates activity 3-fold, while FMN had no effect. This indicates that FAD is a redox cofactor while FMN is not. $Fe^{++}$ showed a stimulatory effect suggesting that iron is a cofactor. The pH optimum of indole oxidation activity in crude SCF was optimal at pH 8.0 (FIG. 3); significant activity (86%) was observed at pH 9.0, but the activity declined rapidly below pH 7.0, with no activity detectable below pH 6.0. The activity was further characterized with respect to rate of indole oxidation as a function of extract concentration used in the oxygraph assay described in Example 11.

Figure 4:
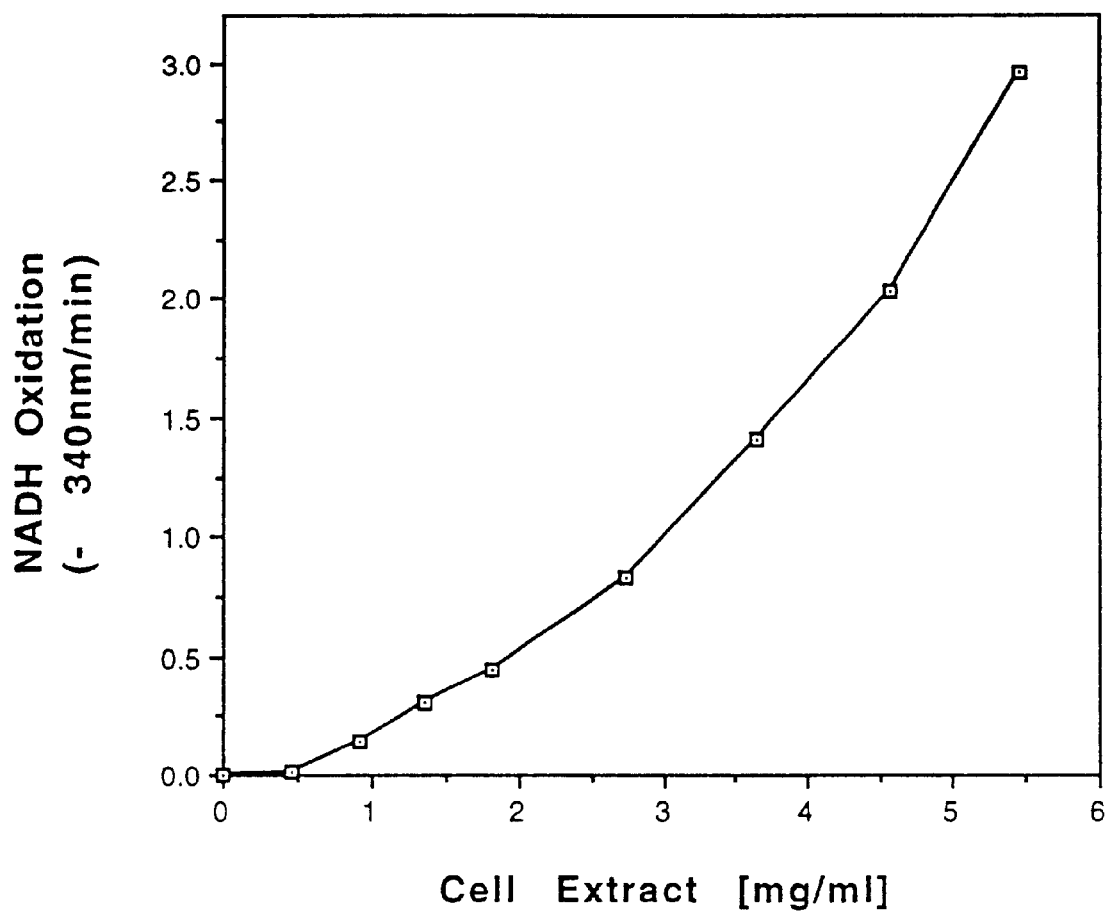
FIG. 4 shows indole-dependent NADH-oxidation using crude protein extract from *P. putida* WW2.
Figure 5:
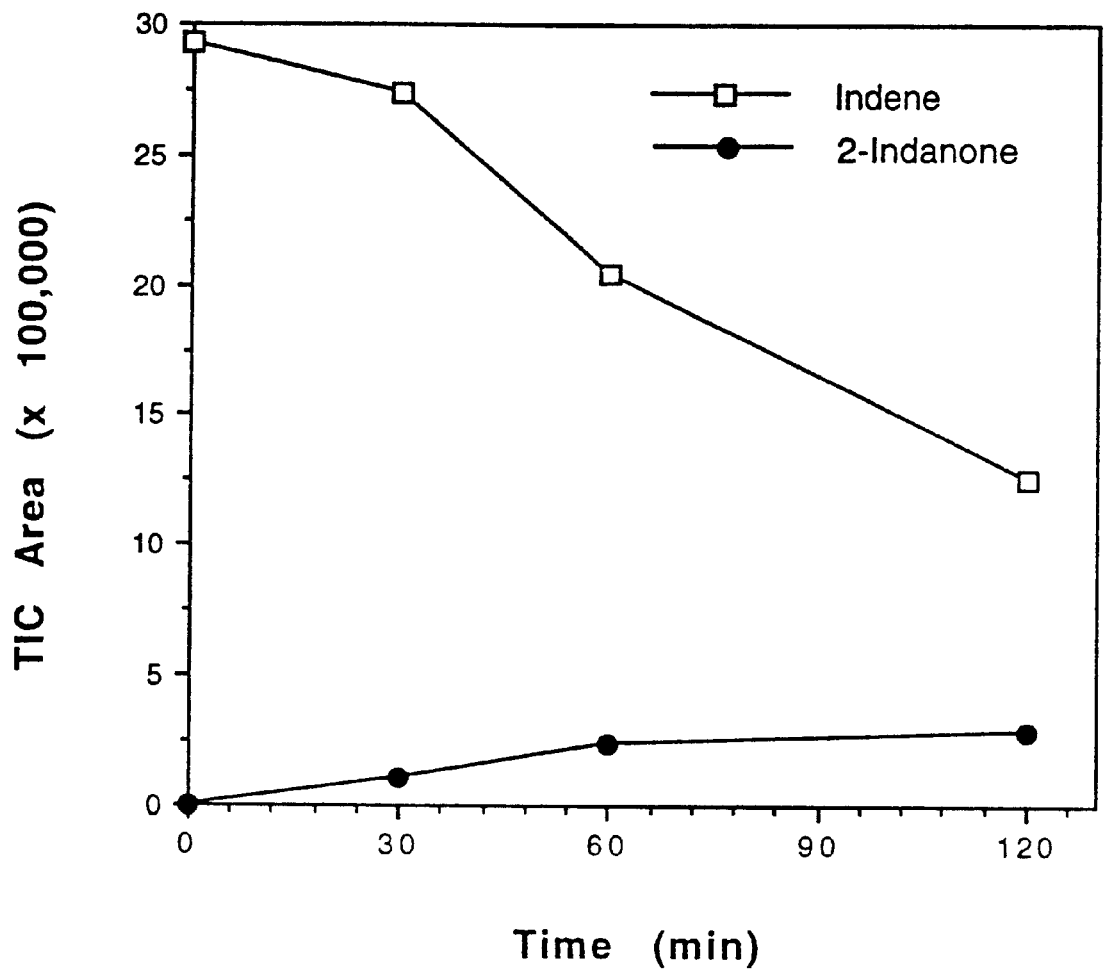
FIG. 5 shows oxidation of indene to 2-indanone by *P. putida* WW2 cell extract with NADPH as the electron donor.

Activity was nonlinear as is shown in FIG. 4. Rate of indole oxidation was greater than linear with increasing enzyme concentration. This data suggests that the heterocyclic oxygenase activity is a multicomponent systerm as are the aromatic ring dioxygenases for toluene (Yeh, W. K., D. T. Gibson, E. Liu (1977) "Toluene dioxygenase: a multi-component enzyme system," *Biochem. Biophys. Res. Commun.* 78:401–410), benzene (Axcell, B. C. and P. J. Geary (1975) "Purification and some properties of a soluble benzene-oxidizing system from a strain of Pseudomonas," *Biochem. J.* 146:173–183), naphthalene (Ensley, B. D., D. T. Gibson, A. L. Laborde (1982) "Oxidation of naphthalene by a multicomponent enzyme system from *Pseudomonas sp.* strain NCIB 9816," *Methods in Enzymology* 188:46–52) and biphenyl (Haddock, J. D., L. M. Nadim, D. T. Gibson (1993) "Oxidation of biphenyl by a multicomponent enzyme system from *Pseudomonas sp.* strain LB400," *J. Bacteriol.* 175:395–400).

Further evidence that the indole oxidizing activity is due to a multicomponent system comes from the partial purification of this activity and is described in Example 8.

EXAMPLE 8

Partial Purification of the Indole Oxidation Activity

Fractionation of crude SCF prepared as described in Example 6 was performed on a BioCad perfusion chromatography workstation (PerSeptive Biosystems, Cambridge, Mass.). Ice cold extract from strain WW2. cells (10 ml, 400 mg protein) was loaded at a flow rate of 5 ml/min onto a column (16 by 150 mm) of Poros HQ anion-exchange media equilibrated with 25 mM Tris-HCl (pH 8.0) buffer. Unbound protein was washed from the column with 10 ml of the same buffer at a flow rate of 25 ml/min. Bound protein was eluted at 25 mi/min with a linear gradient of 0 to 1 M KCl, and 10 ml fractions were collected. The entire chromatography required less than 30 min. Fractions were immediately chilled to 4° C. and assayed for cytochrome c reduction activity as described in the Materials and Methods section above. Cytochrome c oxidizing activity could be identified in the early part of the salt gradient. These fractions were then re-assayed individually and in combination with other fractions for indole-dependent oxygen uptake activity in the presence of NADH as described in Example 11. In this manner a set of fractions capable of reconstituting indole oxygenase activity could be identified. When these fractions were pooled, dialyzed (membrane MWCO: 6,000–8,000) against 25 mM Tris-HCl (pH 8.0) at 4° C. and reapplied to the same column and eluted under the previous elution conditions, additional separation of the cytochrome c oxidase activity and indole oxidizing activity was obtained. The observation that two separate fractions had to be mixed for indole oxidation confirmed the kinetic result described in Example 7 that the enzyme is a multicomponent enzyme system.

EXAMPLE 9

Conversion of Indole to Indigo by Cell Extract

This example shows that the indole oxidase of *Pseudomonas putida* strain WW2 is capable of forming a precursor to indigo. Cell extract (0.57 mg/ml) prepared as in Example 6 and assayed for substrate depletion as described in the Materials and Methods section above (pH 8) was capable of rapidly removing indole from reaction mixtures in the presence of 4.0 mM NADH. No oxidation products were detected in ethyl acetate extracts analyzed by GC/MS (for method see the Materials and Methods section above) nor was any color detected by visual inspection. Identical reactions containing 4.0 mM NADPH instead of NADH removed indole at a rate which was approximately 60% of that observed with NADH. This reaction mixture turned blue in color within 30 min of incubation. The blue color intensified over time. After indole was completely consumed the reaction mixture was diluted into dimethylformamide (DMF) and the visible spectrum of the resultant blue solution was measured. An absorption maximum at 610 nm, identical to that of an authentic sample of indigo, was apparent. Based on this spectral data, it can be concluded that indole was converted to indigo in 20% yield under these experimental conditions.

As noted in Example 7, the oxidase can use either NADH or NADPH as source of reducing equivalents. The observation of indigo formation in the presence of NADPH but not in the presence of NADH, while indole is consumed in both cases, suggests that the absence of $NAD^+$ creates a metabolic block in the pathway allowing a precursor of indigo (spontaneously formed from indoxyl) to accumulate. Indolediol or indoxyl, both potential primary products of the putative indole oxidase/dioxygenase would satisfy this precursor relationship. Metabolic blocks created by the lack of the appropriate nicotinamide dinucleotide has precedent in cis-dihydrodiol dehydrogenases for toluene (Rogers and Gibson (1977) *J. Bacteriology* 130:1117–1124, biphenyl (Haddock et al. (1993) *J. Bacterioloqy* 175:395–400), naphthalene (Jeffrey et al. (1975) *Biochemistry* 11:575–583) and benzenedihydrodiols (Axcell and Geary (1973) *Biochemical J.* 136:927–934) all of which are $NAD^+$ specific. This observation shows that the indole oxidase from *Pseudomonas putida* strain WW2 is capable of oxidizing indole to a precursor of indigo.

EXAMPLE 10

Oxidation of Indene by Cell Extract

As a diagnostic reaction to assess similarities or differences between aromatic dioxygenases from the present heterocyclic indole oxidase, crude SCF as prepared in Example 6 was tested in its ability to oxidatively transform indene. This was carried out under conditions identical to those described in Example 9 for indigo accumulation. Indene removal from reaction mixtures was evident from GC/MS analyses (see Materials and Method Section above). A single detectable product accumulated constituting approximately 20% of the total ion current. This product had a retention time of 7.5 min and its mass spectrum exhibited a molecular ion at m/z=132. Both the retention time and mass spectrum of this product were identical to those of authentic 2-indanone. The identification of 2-indanone as the sole product from indene demonstrates a major difference between the indole oxidation activity in strain WW2 and the well characterized toluene and naphthalene dioxygenase systems. The latter have been shown to oxidize indene to cis-1,2-indandiol and 1-indenol in about equal amounts (Gibson, D. T., S. M. Resnick, K. Lee, J. M. Brand, D. S. Torok, L. P. Wackett, M. J. Schocken, B. E. Haigler (1995) "Desaturation, dioxygenation and monooxygenation reactions catalyzed by naphthalene dioxygenase from *Pseudomonas sp.* strain 9816-4," *J. Bacteriol.* 177:2615–2621). Neither toluene nor naphthalene dioxygenase form 2-indanone. It is also notable that the 2-indanone formed by strain WW2 SCF accumulates and does not appear to be further oxidized. Naphthalene dioxygenase has been shown to oxidize 2-indanone to 2-hydroxy-1-indanone (Resnick, S. M., D. S. Torok, K. Lee, J. M. Brand, D. T. Gibson (1994) "Regiospecific and stereoselective hydroxylation of 1-indanone and 2-indanone by naphthalene dioxygenase and toluene dioxygenase," *Appl. Environ. Microbiol.* 60:3323–3328); this product was not observed in the present study.

EXAMPLE 11

Oxygen Uptake Analysis

Indole oxidation activity in whole cells was routinely determined by measuring oxygen uptake rates with a Biological Oxygen Monitor (Yellow Springs Instrument Co., model 5300, Ohio) equipped with a Clark electrode. Reactions were carried out in a stirred, 1.5 ml reaction chamber at 25° C. Washed cells of strain WW2 suspended in 50 mM Tris-HCl (pH 7.5) to an A600 of 2.0 were pre-equilibrated at 25° C. before their addition to the reaction chamber. After recording the endogenous oxygen uptake rate, indole or other substrates (100 mM in dimethylformamide) were added to a final concentration of 0.3 to 1 mM. This concentration of substrate was saturating; adding higher substrate concentrations did not elevate oxygen consumption, and in some cases higher substrate concentrations (>1.0 mM) were inhibitory to endogenous respiration. Reported rates were corrected for oxygen uptake observed in the absence of substrate. In the case of indoxyl, the reported rate was also corrected for the spontaneous oxygen consumption rate of indoxyl oxidation in the absence of indole-induced cells.

Cell-free indole-dependent oxygen uptake was similarly measured in the same apparatus containing air-saturated 50 mM Tris-HCl (pH 7.5), crude SCF, 1.0 mM NADH and 0.3 mM indole. Other substrates were supplied from DMF stock solutions as described above. Indole-dependent oxygen uptake by fractionated SCF was measured identically except that 1 $\mu$M FAD was supplied prior to the addition of indole. Results are shown in Table 4.

TABLE 4

Cell-Free Oxygen Uptake in WW2 Indole-Induced Cell Extract with Indole, Substituted Indoles and Related Substrates[5]

| Substrate (0.3 mM) | Oxygen Uptake ($O_2$ %/min/ODU) | Relative % | Color |
|---|---|---|---|
| Indole | 14.5 | 100% | — |
| 3-Me-Indole | 2 | 14% | — |
| 4-Cl-Indole | 0 | 0% | — |
| 4-Me-Indole | 1 | 7% | — |
| 4-OH-Indole | 2.5 | 17% | brown |
| 5-OH-Indole | 3.5 | 24% | — |
| 5-MeO-Indole | 1 | 7% | — |
| 5-F-Indole | 13.5 | 93% | — |
| 5-Cl-Indole | 4 | 28% | blue |
| 5-Br-Indole | 0 | 0% | — |
| 5-NO$_2$-Indole | 0 | 0% | — |
| 6-Cl-Indole | 7 | 48% | pink |
| 7-Me-Indole | 12.5 | 86% | — |
| Isatin | 0 | 0% | — |
| Oxindole | 0 | 0% | — |
| Thianaphthene | 1 | 7% | — |
| 2,3-Benzofuran | 0 | 0% | — |

[5]Reactions contained 1.82 mg/ml cell extract protein, 1 mM NADH and 0.3 mM substrate (added in 5 $\mu$l DMF) in 50 mM Tris-HCl (pH 7.5). Reported rates are corrected for oxygen uptake observed in the absence of substrate.

The rates reported reflect the substrate-dependent oxygen uptake rate (corrected for oxygen uptake observed in the absence of substrate). The pH optimum for indole oxidation activity was determined by assaying 150 $\mu$l of crude SCF (2.73 mg protein) in 50 mM sodium phosphate buffer with pH ranging from 5.5 to 7.5 and in 50 mM Tris-HCl with pH ranging from 7.5 to 9.0 (see FIG. 3).

What is claimed:

1. An isolated culture obtainable from *Pseudomonas putida* ATCC #55763.

2. An isolated microorganism which is *Pseudomonas putida* strain ATCC #55763.

3. A cell extract comprising indole oxidizing activity wherein said cell extract comprises cells of *Pseudomonas putida* ATCC #55763 and said indole oxidizing activity is characterized by the oxidation of indole to indoxyl or indolediol in the presence of i) indole; ii) nicotinamide adenine dinucleotide (NADH) or nicotinamide adenine phosphate dinucleotide (NADPH), and iii) flavin adenine dinucleotide (FAD) or $Fe^{+2}$ as a cofactor.

4. The cell extract of claim 3, wherein indole oxidizing activity is characterized by the oxidation of indole to indoxyl or indolediol in the presence of NADH and FAD.

5. The cell extract of claim 3, wherein the indole oxidizing activity is characterized by having a pH optimum of from about 7–9.

6. A process for the production of indoxyl or indigo in a *Pseudomonas putida* ATCC No. 55763, the process comprising a) cultivating the *P. putida* ATCC No. 55763 in the presence of indole under conditions facilitating the endogenous or exogenous expression of indole oxidase activity to convert indole to indolediol, and b) blocking any, or substantially any, enzymatic conversion of said indolediol to dihydroxyindole in the *P. putida* ATCC No. 55763, wherein said enzymatic conversion of indolediol to dihydroxyindole is blocked by the mutation or deletion of a gene encoding dehydrogenase activity.

* * * * *